(12) United States Patent
Tinnemans et al.

(10) Patent No.: US 10,133,192 B2
(45) Date of Patent: Nov. 20, 2018

(54) METHOD AND APPARATUS FOR DETERMINING THE PROPERTY OF A STRUCTURE, DEVICE MANUFACTURING METHOD

(71) Applicant: ASML Netherlands B.V., Veldhoven (NL)

(72) Inventors: Patricius Aloysius Jacobus Tinnemans, Hapert (NL); Simon Gijsbert Josephus Mathijssen, Rosmalen (NL); Sander Bas Roobol, Veldhoven (NL); Nan Lin, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/494,056

(22) Filed: Apr. 21, 2017

(65) Prior Publication Data
US 2017/0315055 A1 Nov. 2, 2017

(30) Foreign Application Priority Data
Apr. 29, 2016 (EP) ..................................... 16167643

(51) Int. Cl.
*G03F 7/20* (2006.01)
*G03F 9/00* (2006.01)
(Continued)

(52) U.S. Cl.
CPC ......... *G03F 7/70616* (2013.01); *G01N 21/47* (2013.01); *G01N 21/8806* (2013.01);
(Continued)

(58) Field of Classification Search
CPC ............... G03F 7/70633; G03F 7/7065; G03F 7/70625; G03F 7/70483; G03F 7/70641;
(Continued)

(56) References Cited

U.S. PATENT DOCUMENTS 9,772,562 B2   9/2017  Mink et al.
2004/0051040 A1  3/2004  Nasu et al.
(Continued)

FOREIGN PATENT DOCUMENTS

EP   1586912 A1   10/2005
JP   2009069073 A   4/2009
(Continued)

OTHER PUBLICATIONS

International Search Report and Written Opinion directed to International Patent Application No. PCT/EP2017/058676, dated Aug. 8, 2017; 26 pages.
(Continued)

*Primary Examiner* — Michelle M Iacoletti
(74) *Attorney, Agent, or Firm* — Sterne, Kessler, Goldstein & Fox P.L.L.C.

(57) ABSTRACT

A structure of interest (T) is irradiated with radiation for example in the x-ray or EUV waveband, and scattered radiation is detected by a detector (19, 274, 908, 1012). A processor (PU) calculates a property such as linewidth (CD) or overlay (OV), for example by simulating (S16) interaction of radiation with a structure and comparing (S17) the simulated interaction with the detected radiation. The method is modified (S14*a*, S15*a*, S19*a*) to take account of changes in the structure which are caused by the inspection radiation. These changes may be for example shrinkage of the material, or changes in its optical characteristics. The changes may be caused by inspection radiation in the current observation or in a previous observation.

19 Claims, 7 Drawing Sheets

(51) Int. Cl.
*G01N 21/47* (2006.01)
*G01N 21/88* (2006.01)
*G01N 21/95* (2006.01)
*G01N 21/956* (2006.01)
*H01L 21/66* (2006.01)

(52) U.S. Cl.
CPC ....... *G01N 21/9501* (2013.01); *G01N 21/956* (2013.01); *G01N 21/95607* (2013.01); *G03F 7/7065* (2013.01); *G03F 7/70625* (2013.01); *G03F 7/70633* (2013.01); *G03F 7/70683* (2013.01); *G03F 9/7003* (2013.01); *H01L 22/12* (2013.01); *G01N 2021/4704* (2013.01); *G01N 2021/4735* (2013.01); *G01N 2021/8822* (2013.01); *G01N 2021/95615* (2013.01); *G01N 2201/12* (2013.01)

(58) Field of Classification Search
CPC ............. G03F 7/70341; G03F 7/70683; G03F 9/7034; G03F 7/7015; G03F 7/70491; G03F 7/705; G03F 7/70608; G03F 7/70616; G03F 9/7019; G03F 9/7049; G03F 9/7088; G01N 2021/4704; G01N 2021/4735; G01N 2021/8822; G01N 21/47; G01N 21/8806; G01N 2201/12
See application file for complete search history.

(56) References Cited

U.S. PATENT DOCUMENTS

| | | |
|---|---|---|
| 2006/0033921 A1 | 2/2006 | Den Boef et al. |
| 2006/0054818 A1 | 3/2006 | Kim |
| 2006/0066855 A1 | 3/2006 | Den Boef et al. |
| 2009/0197189 A1 | 8/2009 | Ide et al. |
| 2010/0201963 A1 | 8/2010 | Cramer et al. |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2011/0102753 A1 | 5/2011 | Van De Kerkhof et al. |
| 2012/0044470 A1 | 2/2012 | Smilde et al. |
| 2012/0123581 A1 | 5/2012 | Smilde et al. |
| 2012/0123748 A1 | 5/2012 | Aben et al. |
| 2012/0182538 A1 | 7/2012 | Koole et al. |
| 2013/0258310 A1 | 10/2013 | Smilde et al. |
| 2013/0271740 A1 | 10/2013 | Quintanilha |
| 2014/0192338 A1 | 7/2014 | Den Boef |
| 2015/0036914 A1 | 2/2015 | Sekiguchi et al. |
| 2015/0046118 A1 | 2/2015 | Pandev et al. |
| 2015/0331336 A1 | 11/2015 | Quintanilha et al. |

FOREIGN PATENT DOCUMENTS

| | | |
|---|---|---|
| JP | 4263556 B2 | 5/2009 |
| JP | 2013242467 A | 12/2013 |
| TW | 201518871 A | 5/2015 |
| TW | 201525412 A | 7/2015 |
| WO | WO 2015/172963 A1 | 11/2015 |
| WO | WO 2017/025373 A1 | 2/2017 |
| WO | WO 2017/025392 A1 | 2/2017 |

OTHER PUBLICATIONS

Hayashi et al., "Study of ADI (After Develop Inspection) on Photo Resist Wafers Using Electron Beam (II)," SPIE, vol. 6518, 2007; 10 pages.

Kawamura et al., "An Analysis of and a Method of Enhancing the Intensity of OBIRCH Signal for Defects Observation in VLSI Metal Interconnections," IEICE Transactions on Electronics, Institute of Electronics, vol. E77-C, No. 4, Apr. 1994; pp. 579-584.

Liu et al., "A physical resist shrinkage model for full-chip lithography simulations," Proc. SPIE, vol. 9779, Advances in Patterning Materials and Processes XXXIII, 97790Y, Mar. 25, 2016; 10 pages.

Jones et al., "Small angle x-ray scattering for sub-100 nm pattern characterization," Applied Physics Letters, The Americna Institute of Physics, vol. 83, No. 19, Nov. 10, 2003; pp. 4059-4061.

Lemaillet et al., "Intercomparison between optical and x-ray scatterometry measurements of FinFET structures," Proc. SPIE, vol. 8681; 8 pages.

METHOD AND APPARATUS FOR DETERMINING THE PROPERTY OF A STRUCTURE, DEVICE MANUFACTURING METHOD

FIELD

The present invention relates to methods and apparatus for simulating interaction of radiation with structures. The invention may be applied for example in metrology of microscopic structures, for example to assess and improve performance of a lithographic, or to determine the structure of a molecule or crystal. The radiation may be electromagnetic radiation of any desired wavelength, but the invention may find particular application where inspection radiation in wavebands shorter than the visible waveband is being used or has been used to inspect a structure. Shorter wavebands include for example UV, DUV, soft x-ray (extreme ultraviolet) and x-ray wavebands.

BACKGROUND

While the invention may be applied to a range of applications, consider as an example the manufacture of semiconductor devices such as integrated circuits (ICs) by a lithographic process. In that instance, a lithographic apparatus is used to apply a pattern of device features to be formed on an individual layer of the IC. This pattern can be transferred onto a target portion (e.g., including part of, one, or several dies) on a substrate (e.g., a silicon wafer).

In lithographic processes, it is desirable frequently to make measurements of the structures created, e.g., for process control and verification. Various tools for making such measurements are known, including scanning electron microscopes (SEM), which are often used to measure properties of a structure, such as the critical dimension (CD). Recently, various forms of scatterometers have been developed for use in the lithographic field. These devices direct a beam of radiation onto a target and measure one or more properties of the scattered radiation as it is reflected and/or transmitted by the target, e.g., intensity at a single angle as a function of wavelength; intensity at one or more wavelengths as a function of angle; or polarization as a function of angle—to obtain a "spectrum" of one form or another. The term "spectrum" in this context will be used with a wide scope. It may refer to a spectrum of different wavelengths (colors), it may refer to a spectrum of different directions (diffraction angles), different polarizations, or a combination of any or all of these. From this spectrum a property of interest of the target can be determined. Compared with SEM techniques, scatterometers can be used with much higher throughput, on a large proportion or even all of the product units. The measurements can be performed very quickly. The time to obtain a measurement result depends on the complexity of the calculations and the processing power available, but can be done off-line. Determination of the property of interest may be performed by various calculation techniques. One particular approach is to perform reconstruction of the target structure by forward modeling of the scattering process, and iterative calculations. In another approach, simulated spectra are calculated in advance for a variety of points in the parameter space. These simulated spectra serve as a "library" which is searched to find a match for a spectrum observed later on a real target.

Frequently the structure is modeled in a parametrized form. Parameters corresponding to the property of interest are considered as "floating" parameters, whose value is (ideally) to be established using the observation data. Other parameters may be fixed. Typically, the property of interest is just one parameter among a number of unknowns, and the model can have many degrees of freedom. Automated methods of optimizing the selection of fixed and floating parameters are described in the prior art, for example in US20120123748.

Examples of known scatterometers include angle-resolved scatterometers of the type described in US2006033921A1 and US2010201963A1. The targets used by such scatterometers are relatively large, e.g., 40 µm by 40 µm, gratings and the measurement beam generates a spot that is smaller than the grating (i.e., the grating is underfilled). In addition to measurement of feature shapes by reconstruction, diffraction based overlay can be measured using such apparatus, as described in published patent application US2006066855A1. If the parameter of interest is an asymmetry-related parameter, such as overlay, a measurement of that parameter can in some cases be obtained relatively directly, based on asymmetry observed in the scatter spectrum. Diffraction-based overlay metrology using dark-field imaging of the diffraction orders enables overlay measurements on smaller targets. Examples of dark field imaging metrology can be found in international patent applications US2014192338 and US2011069292A1 which documents are hereby incorporated by reference in their entirety. Further developments of the technique have been described in published patent publications US20110027704A, US20110043791A, US2011102753A1, US20120044470A, US20120123581A, US20130258310A and US20130271740A. These targets can be smaller than the illumination spot and may be surrounded by product structures on a wafer. Multiple gratings can be measured in one image, using a composite grating target. The contents of all these applications are also incorporated herein by reference.

Prior commercial scatterometers use inspection radiation in the visible and infrared wavebands. As the sizes of features produced by lithography shrink ever smaller and dimensional tolerances shrink accordingly, there is an interest in the use of diffraction based techniques (scatterometry) at shorter wavelengths, such as UV, DUV, "soft x-ray" (extreme ultraviolet) and even x-ray wavelengths. Scattering of electromagnetic waves can be simulated by use of Maxwell's equations at such short wavelengths in the same way as at longer wavelengths. This approach is used to analyze x-ray diffraction patterns from all field of physics: power diffraction, crystallography, biology, etc. In semiconductor manufacturing, reconstruction of critical dimension using small-angle x-ray scattering (CD-SAXS) is already known. Examples are, for example, P. Lemaillet et al, "Intercomparison between optical and x-ray scatterometry measurements of FinFET structures" Metrology, Inspection, and Process Control for Microlithography XXVII, Proc. of SPIE Vol. 8681, 2013 or Ronald L. Jones, et al."Small angle x-ray scattering for sub-100 nm pattern", Appl. Phys. Lett. 83, 4059 (2003).

Examples of transmissive and reflective metrology techniques using these wavelengths in transmissive and/or reflective scattering modes are disclosed in pending patent applications PCT/EP2015/058238 filed 16 Apr. 2015, EP15180807.8 filed 12 Aug. 2015 and EP15180740.1 filed 12 Aug. 2015, not published at the present priority date. The contents of all these applications are incorporated herein by reference. In addition to reconstruction and other techniques, asymmetry measurements can be made in scatter spectra, whatever the wavelength.

Conventional techniques naturally assume that the structure under inspection remains constant in shape and composition during an exposure(s) to capture one or more spectra. In the x-ray and EUV range of the electromagnetic spectrum (and sometimes in the DUV, UV and even the visible part of the spectrum) many materials are actually changed to some extent by the inspection radiation. Properties of a material in the structure may change in the course of the observation, and the dimensions of the structure may change. Whenever a property of the structure changes, the measurement of a property of interest may be affected in the same way as a photograph is affected by a subject moving in the course of a long exposure. Changes in one property may influence the result of reconstruction or other measurement techniques, even if the changing parameter is not the parameter of interest.

A well-known example of such changes is the phenomenon of resist shrinkage, which has been observed in lithographic patterning steps performed using EUV radiation. One study derives a model of resist shrinkage, as reported in Peng Liu Leiwu Zheng, Maggie Ma, Qian Zhao, Yongfa Fan, et al. "A physical resist shrinkage model for full-chip lithography simulations", Proc. SPIE 9779, Advances in Patterning Materials and Processes XXXIII, 97790Y (Mar. 25, 2016); doi:10.1117/12.2239243. The authors in that paper report on modeling of changes occurring in the resist during exposure, prior to development. The paper does not discuss changes that could occur in the resist pattern (or other material), in the course of inspection of the pattern after it has been produced.

SUMMARY OF THE INVENTION

The invention aims to allow greater accuracy in determining property of a structure, even when interactions of the inspection radiation causes the structure to change in some way over the course of an exposure. In most cases, what is of interest is the state of the structure as it exists prior to the measurement.

The invention in a first aspect provides a method of simulating interaction of radiation with a structure, the method including the steps of:
(a) defining one or more variable parameters to represent the structure, the variable parameters including at least one parameter of interest;
(b) receiving observation data obtained by exposing the structure one or more times with inspection radiation and observing said inspection radiation after interaction with the structure; and
(c) based on the observation data, determining a value for the parameter of interest as a property of the structure, wherein the determination of the parameter of interest is performed taking into account changes in the structure caused by the inspection radiation during an exposure period.

The method can be used as part of a metrology method. The method may be one which uses simulated interactions for reconstruction of the structure. In such a case, the variable parameters may include one or more time-related parameters representing said changes in the structure caused by the inspection radiation during said exposure period. The method may include determining a value for one or more time-related parameters, as part of determining a value for a parameter of interest.

In other embodiments, a single parameter of interest may be derived more or less directly from the observed radiation, and a simple correction may be included to adjust for an assumed change in the structure. As an example, asymmetry may be a parameter of interest, which can be measured more or less directly from asymmetry observed in the inspection radiation after it has interacted with the structure. To do this, however, calibration is required. According to the present invention, this calibration can take into account changes caused by the inspection radiation of the current observation or some previous observation.

The method can be applied also in a metrology method based on machine learning. In this type of approach, a processor may be trained with many examples of structures and corresponding observed spectra, to find directly the relationship between the observed spectra and the shape and composition of the target structure.

The determination of the parameter of interest is performed taking into account changes in the structure caused by inspection radiation during an exposure period related a current observation or to a previous observation of the same structure. For example, a target structure may be observed successively under different illumination conditions to obtain measurements of different parameters of interest, or a single parameter of interest. An observation may simply be repeated to obtain higher accuracy. By applying the principles of the present disclosure, the results of a current observation can be corrected to take account of the effects of the radiation used for a previous observation, whether or not that inspection radiation has the same characteristics as the inspection radiation used in the current observation.

The invention further provides a processing apparatus for determining parameters of a structure, the processing apparatus comprising:
storage for one or more variable parameters to represent the structure, the variable parameters including at least one parameter of interest;
storage for receiving observation data obtained by exposing the structure one or more times with inspection radiation and observing said inspection radiation after interaction with the structure; and
a processor arranged to use the observation data to determine a value for the parameter of interest as a property of the structure, taking into account changes in the structure caused by the inspection radiation during an exposure period.

The invention yet further provides a metrology apparatus for use in determining parameters of a structure, the metrology apparatus comprising:
an illumination system for generating a beam of inspection radiation;
a substrate support operable with the illumination system for irradiating a structure formed on the substrate with said inspection radiation;
a detection system for detecting the inspection radiation after interaction with the structure; and
a processing apparatus as claimed in claim arranged to determine a property of the structure based on the detected radiation and taking into account changes in the structure caused by the inspection radiation during an exposure period.

The processing apparatus may be provided for performing a method according to the invention as set forth above. The processing apparatus and/or method may be implemented by running a suitable program of instructions on a computer. The instructions may form a computer program product. The instructions may be stored in a non-transitory storage medium.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Embodiments of the invention will now be described, by way of example, with reference to the accompanying drawings in which.

Figure 5:
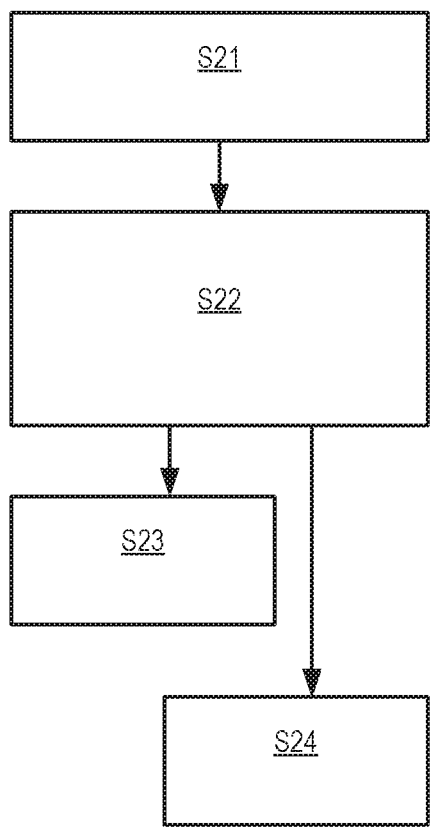
FIG. 5 is a flow chart illustrating a method of controlling performance of a metrology method and/or of a lithographic manufacturing process using measurements made by the method of FIG. 4.
Figure 6A:
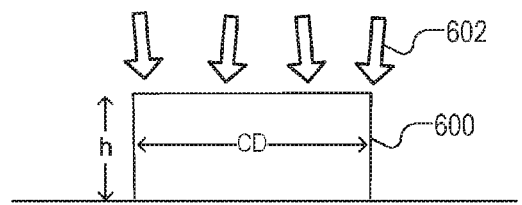
Figure 6B:
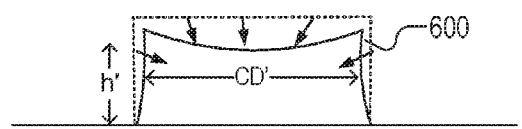
Figure 7A:
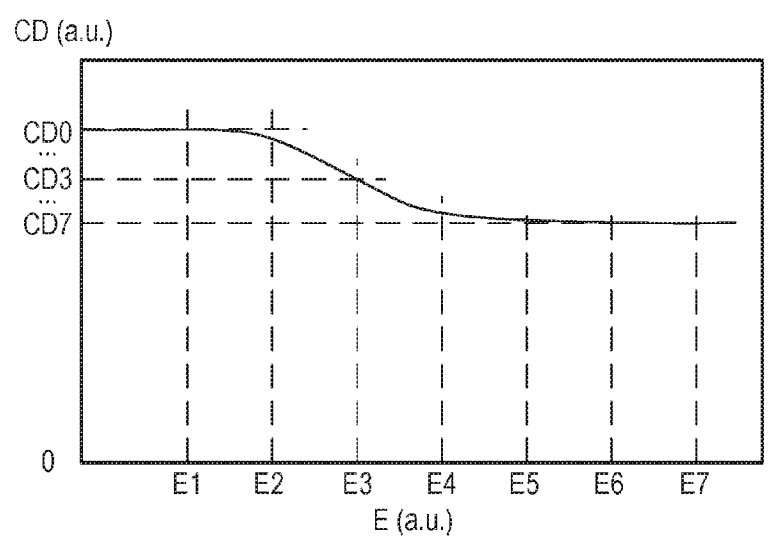
Figure 7B:
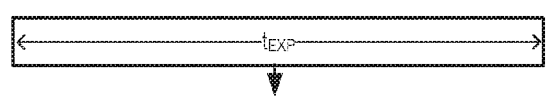
Figure 7C:
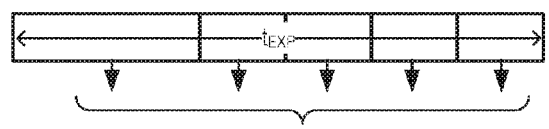
Figure 8:
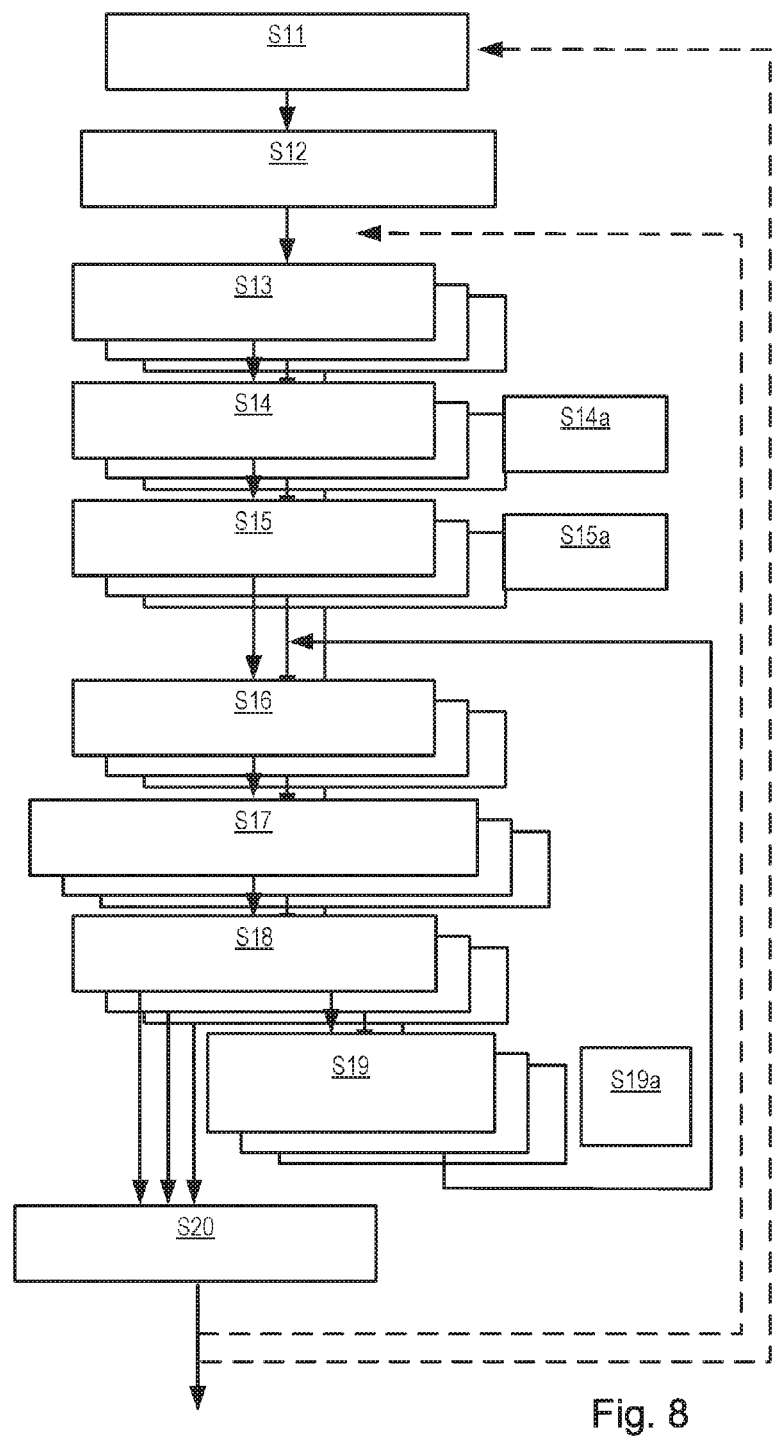
Figure 9:
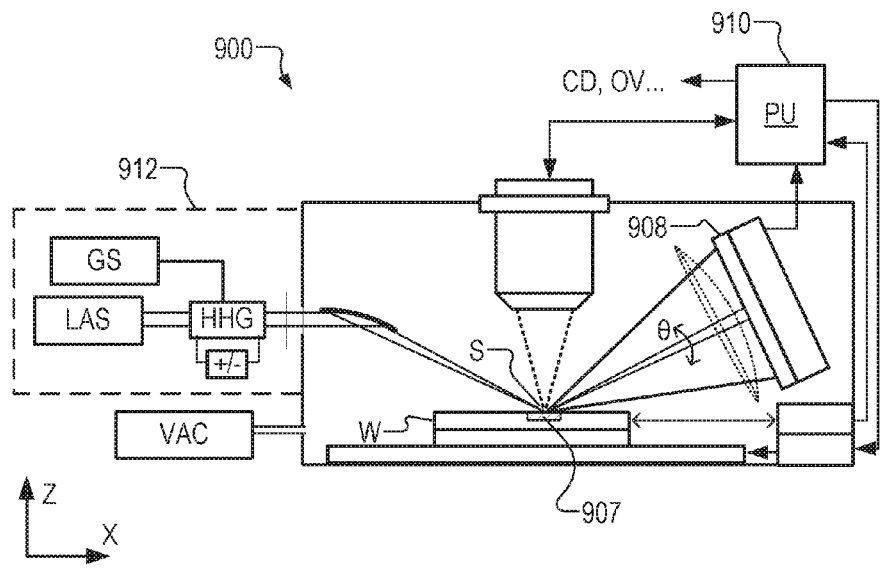
Figure 10:
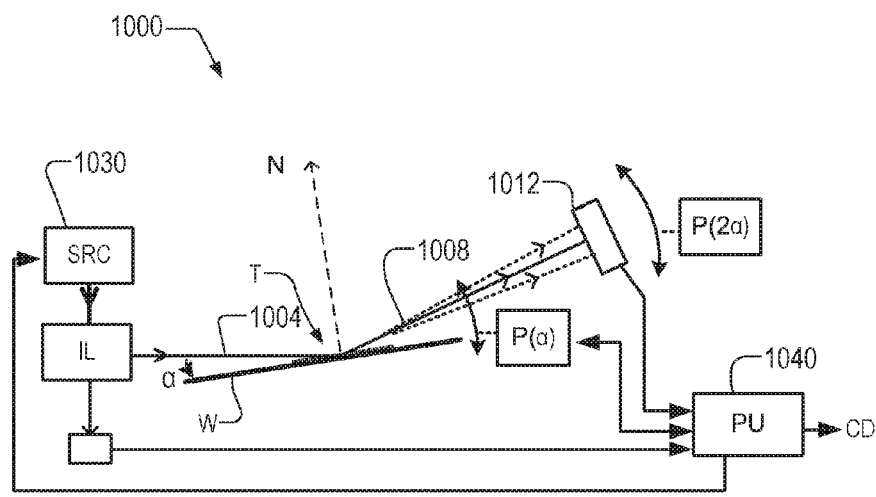

FIGS. 6(a) and 6(b) illustrate the phenomenon of resist shrinkage, as an example of a change that can occur in a structure under inspection radiation;

FIG. 7(a) illustrates an example of the changes of a dimensional parameter under different doses of inspection radiation;

FIG. 7(b) illustrates an exposure period corresponding to a single captured spectrum;

FIG. 7(c) illustrates the sub-dividing of the exposure period to capture separate spectra;

FIG. 8 is a flowchart illustrating a modification of the method of FIG. 5, corresponding to the example of FIG. 7(c);

FIG. 9 illustrates schematically an apparatus for performing lensless imaging using EUV radiation reflected from a target structure; and FIG. 10 illustrates schematically a metrology apparatus based on reflection of x-ray and/or EUV radiation using an inverse Compton scattering source.

DETAILED DESCRIPTION OF EXEMPLARY EMBODIMENTS

Before describing embodiments of the invention in detail, it is instructive to present an example environment in which embodiments of the present invention may be implemented.
Lithographic Manufacturing Background FIG. 1 at 200 shows a lithographic apparatus LA as part of an industrial facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables WTa and WTb and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system which receives some or all of the substrates W that have been processed in the litho cell. Metrology results are provided directly or indirectly to the supervisory control system (SCS) 238. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Figure 1:
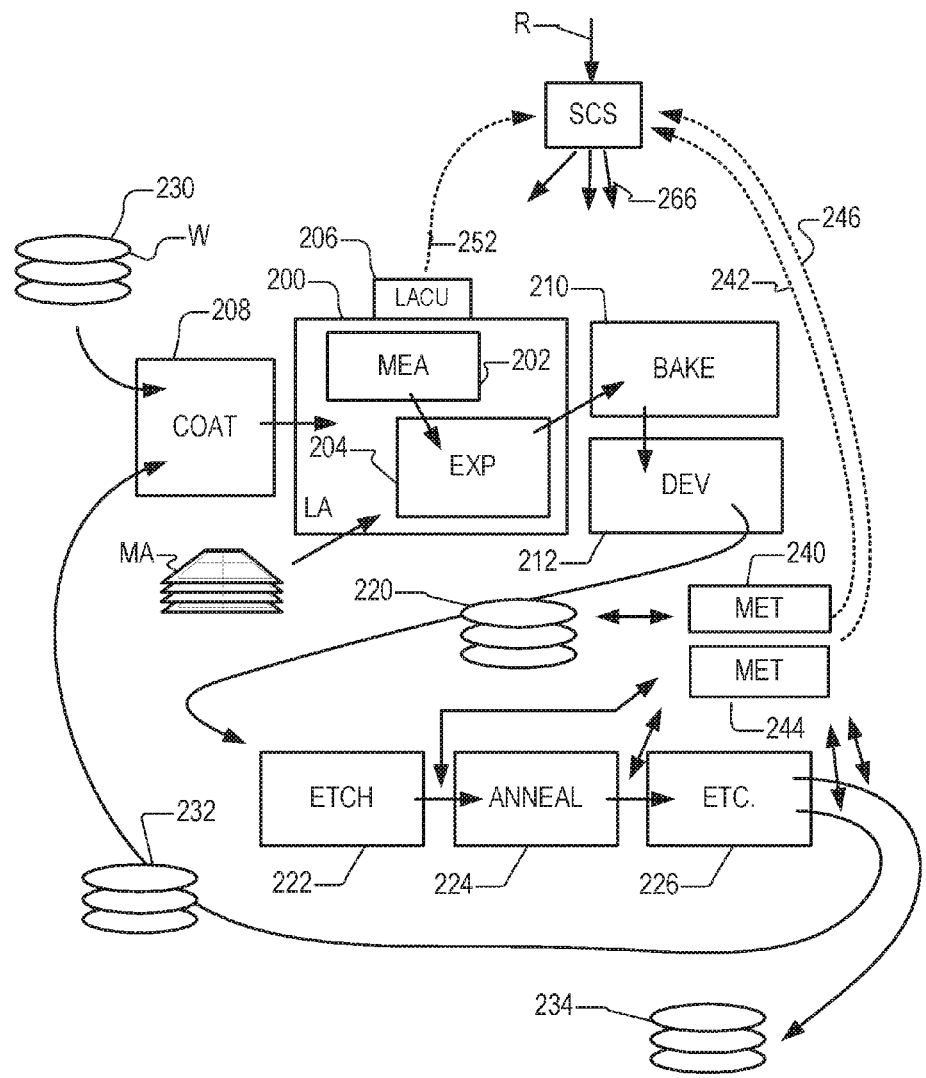
FIG. 1 depicts a lithographic apparatus together with other apparatuses forming a production facility for semiconductor devices.

Also shown in FIG. 1 is a metrology apparatus 240 which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 220 prior to etching in the apparatus 222. Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

Each generation of lithographic manufacturing technology (commonly referred to as a technology "node") has smaller feature sizes and tighter specifications for performance parameters such as CD. Therefore metrology apparatus using shorter wavelengths of radiation is increasingly considered as a solution to improve the resolution of measurements. The metrology apparatus 240 may be adapted to use shorter wavelengths, such as UV, DUV, EUV (soft x-ray) or even x-ray wavelengths. More specifically, such a metrology apparatus may be operating at wavelengths below 400 nm, optionally below 200 nm, below 100 nm, below 10 nm or below 1 nm. Product features and/or product-like features can be measured directly, even at the smallest technology nodes, and in-die targets can be provided and measured without losing too much area. In another implementation, which is the example illustrated in FIG. 1, the metrology apparatus 240 is a conventional optical scatterometer using inspection radiation in the infrared and visible parts of spectrum. In addition, however, the manufacturing system includes one or more metrology apparatuses 244 operating in one or more of the shorter wavelength ranges mentioned above. This additional metrology apparatus provides additional metrology results 246 which can be used by supervisory control system SCS to achieve further control of quality and improvement in performance of the lithographic manufacturing system as a whole.

The metrology apparatuses 240 and 244 can be used independently of one another, or can be used together to make a kind of hybrid metrology system. For example, an optical scatterometer can be used to inspect structures within the resist material treated within the litho cell, and the additional metrology apparatus 244 can be used for the same purpose. Additionally, an optical or x-ray metrology apparatus may be applied to measure structures after they have been formed in harder material. For example, substrates may be inspected using additional metrology apparatus 244 after they have been processed by the etching apparatus 222, annealing apparatus 224 and/or other apparatus 226. The present disclosure is not limited to any particular wavelength range, nor to measurement of structures at any particular stage of the manufacturing process.

Metrology Introduction

Figure 2:
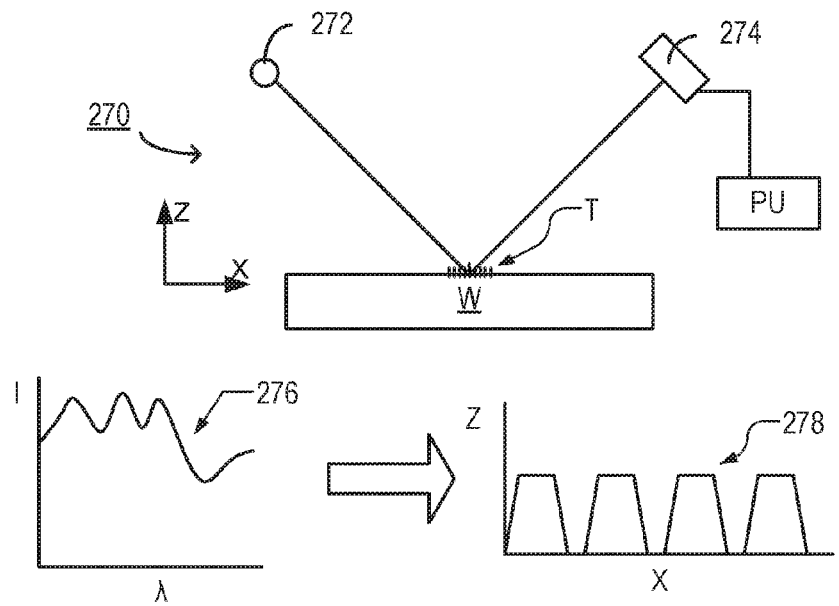
FIG. 2 illustrates the principles of operation of a spectroscopic scatterometer as a first example of an inspection apparatus.

FIG. 2 depicts a spectroscopic scatterometer 270 which may be used as an inspection apparatus in a metrology system of the type described above. The spectroscopic scatterometer may be of a known design, or of a new design. Using the system of FIG. 1 as an example, the spectroscopic scatterometer 270 may be used as the metrology apparatus 240 with UV, visible or infrared wavelengths. When adapted for use with UV, DUV or soft x-ray or x-ray radiation, the spectroscopic scatterometer 270 can be used as the additional metrology apparatus 244.

Spectroscopic scatterometer 270 comprises a broadband radiation projector 272 which projects inspection radiation onto a substrate W. Radiation reflected or diffracted by a target structure T is passed to a spectrometer 274, which measures a spectrum 276 (intensity as a function of wavelength) of the specular reflected or diffracted radiation. From this data, the structure or profile 278 giving rise to the detected spectrum may be reconstructed by calculation within processing unit PU. The reconstruction can be performed for example by Rigorous Coupled Wave Analysis and non-linear regression, or comparison with a library of pre-measured spectra or pre-computed simulated spectra. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 3:
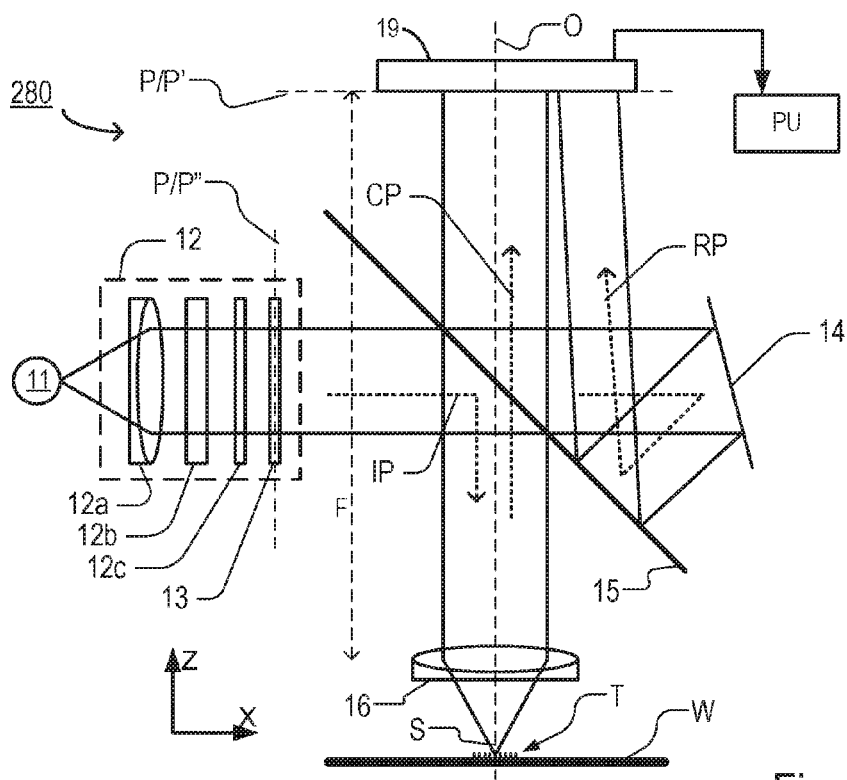
FIG. 3 illustrates in schematic form an angle-resolved scatterometer as another example of an inspection apparatus.

FIG. 3 shows the basic elements of an angle-resolved scatterometer 280 that may be used instead of or in addition to a spectroscopic scatterometer 270. Angle-resolved scatterometer 280 may be of a known design or of a new design. Using the system of FIG. 1 as an example, angle-resolved scatterometer may be used with UV, visible or infrared wavelengths as the metrology apparatus 240 in the system FIG. 1. When adapted for use with UV, DUV or soft x-ray or x-ray radiation, the spectroscopic scatterometer can be used as the additional metrology apparatus 244.

In this type of scatterometer, radiation emitted by a radiation source 11 is conditioned by an illumination system 12. For example, illumination system 12 may include a collimating using lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired. Further increases in NA can be obtained by use of solid immersion lens (SIL) techniques, including micro-SIL and equivalents.

As in the lithographic apparatus LA, one or more substrate tables may be provided to hold the substrate W during measurement operations. (In an example where the inspection apparatus is integrated with the lithographic apparatus, they may even be the same substrate tables.) Various sensors and actuators are provided for example to acquire the position of a target of interest, and to bring it into position under the objective lens 16. Typically many measurements will be made on targets at different locations across substrate W. The substrate support can be moved in X and Y directions to acquire different targets, and in the Z direction to obtain a desired focusing of the optical system on the target. It is convenient to think and describe operations as if the objective lens and optical system are being brought to different locations on the substrate, when in practice the optical system remains substantially stationary and only the substrate moves. Provided the relative position of the substrate and the optical system is correct, it does not matter in principle whether one or both of those is moving in the real world.

When the radiation beam is incident on the beam splitter 16 part of it is transmitted through the beam splitter (partially reflecting surface 15) and follows a reference path RP towards a reference mirror 14.

Radiation reflected by the substrate, including radiation diffracted by any metrology target T, is collected by lens 16 and follows a collection path CP in which it passes through partially reflecting surface 15 into a detector 19. The detector may be located in the back-projected pupil plane P, which is at the focal length F of the lens 16. In practice, the pupil plane itself may be inaccessible, and may instead be re-imaged with auxiliary optics (not shown) onto the detector located in a so-called conjugate pupil plane P'. The detector may be a two-dimensional detector so that a two-dimensional angular scatter spectrum or diffraction spectrum of a substrate target 30 can be measured. In the pupil plane or conjugate pupil plane, the radial position of radiation defines the angle of incidence/departure of the radiation in the plane of focused spot S, and the angular position around an optical axis O defines azimuth angle of the radiation. The detector 19 may be, for example, an array of CCD or CMOS sensors, and may use an integration time of, for example, 40 milliseconds per frame.

Radiation in reference path RP is projected onto a different part of the same detector 19 or alternatively on to a different detector (not shown). A reference beam is often used for example to measure the intensity of the incident radiation, to allow normalization of the intensity values measured in the scatter spectrum.

Returning to the known apparatus, the various components of illumination system 12 can be adjustable to implement different metrology 'recipes' within the same apparatus. Color filter 12b may be implemented for example by a set of interference filters to select different wavelengths of interest in the range of, say, 405-790 nm or even lower, such as 200-400 nm, 100-200 nm, 1-100 nm or 0.01 to 1 nm. (Operation at these lower wavelengths require modified optical systems, but the principles of operation are the same.) An interference filter may be tunable rather than comprising a set of different filters. A grating could be used instead of interference filters. Polarizer 12c may be rotatable or swappable so as to implement different polarization states in the radiation spot S. Aperture device 13 can be adjusted to implement different illumination profiles. Aperture device 13 is located in a plane P'' conjugate with pupil plane P of objective lens 16 and the plane of the detector 19. In this way, an illumination profile defined by the aperture device defines the angular distribution of light incident on substrate radiation passing through different locations on aperture device 13.

The detector 19 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic-polarized light and transverse electric-polarized light.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. This pattern is sensitive to aberrations in the lithographic projection apparatus, particularly the projection system PS. Illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes. The techniques disclosed herein are not limited to inspection of grating structures, and any target structure, including a blank substrate or a substrate having only flat layers on it, is included within the term "target structure"

In addition to measurement of parameters by reconstruction, angle resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement using the instrument of FIG. 3 are described for example in published patent application US2006066855A1 cited above. Simply stated, while the positions of the diffraction orders in the diffraction spectrum of the target are determined only by the periodicity of the target, asymmetry of intensity levels in the diffraction spectrum is indicative of asymmetry in the individual features which make up the target. In the instrument of FIG. 3, where detector 19 may be an image sensor, such asymmetry in the diffraction orders appears directly as asymmetry in the pupil image recorded by detector 19. This asymmetry can be measured by digital image processing in unit PU, and calibrated against known values of overlay.

In a further development of the angle-resolved scatterometer, a field image sensor (not shown) may be provided and used to measure asymmetry in smaller targets using so-called dark-field imaging. For example in a known apparatus, a second beam splitter divides the collection path into two branches, one for pupil imaging and one for dark-field imaging. In a first measurement branch, detector 19 records a scatter spectrum or diffraction spectrum of the target exactly as described above. This detector 19 may be referred to as the pupil image detector. In the dark-field imaging measurement branch (not shown here), an imaging optical system forms an image of the target on the substrate W on another sensor (e.g. a CCD or CMOS sensor). This other sensor can be referred to as the field image sensor. An aperture stop is provided in a plane that is in the collection path in a plane conjugate to the pupil-plane (it may also be called a pupil stop). This aperture stop functions to block the zeroth order diffracted beam so that the image of the target formed on the field image sensor is formed only from the first order beam(s). This is the so-called dark field image, equivalent to dark field microscopy. The images captured by one or both sensors are output to image processor and controller PU, the function of which will depend on the particular type of measurements being performed.

While the known examples provide pupil image sensor and field image sensor in separate branches of an optical system, another apparatus might have only a pupil image sensor or a field image sensor. Alternatively, movable optical elements may be provided so that the same image sensor 19 can be used sometimes as a pupil image sensor and sometimes as a field image sensor. In any case, the principles of the present disclosure may be applied in any type of metrology apparatus using inspection radiation, whether for scatterometry or imaging, direct imaging or dark-field imaging, While the scatterometers of FIGS. 2 and 3 are illustrated schematically as comprising transmissive (refractive) optical elements, the skilled person will appreciate that some or all of these elements may in practice be reflective elements. This is particularly the case when UV and shorter wavelengths of inspection radiation are chosen for use. Examples of such apparatus will be described below, with reference to FIGS. 9 and 10. While the examples illustrated herein use radiation scattered upon reflection by the target structure, other implementations, for example at x-ray wavelengths (below, say 1 nm), may use radiation scattered upon transmission by the structure.

Introduction to Reconstruction

Figure 4:
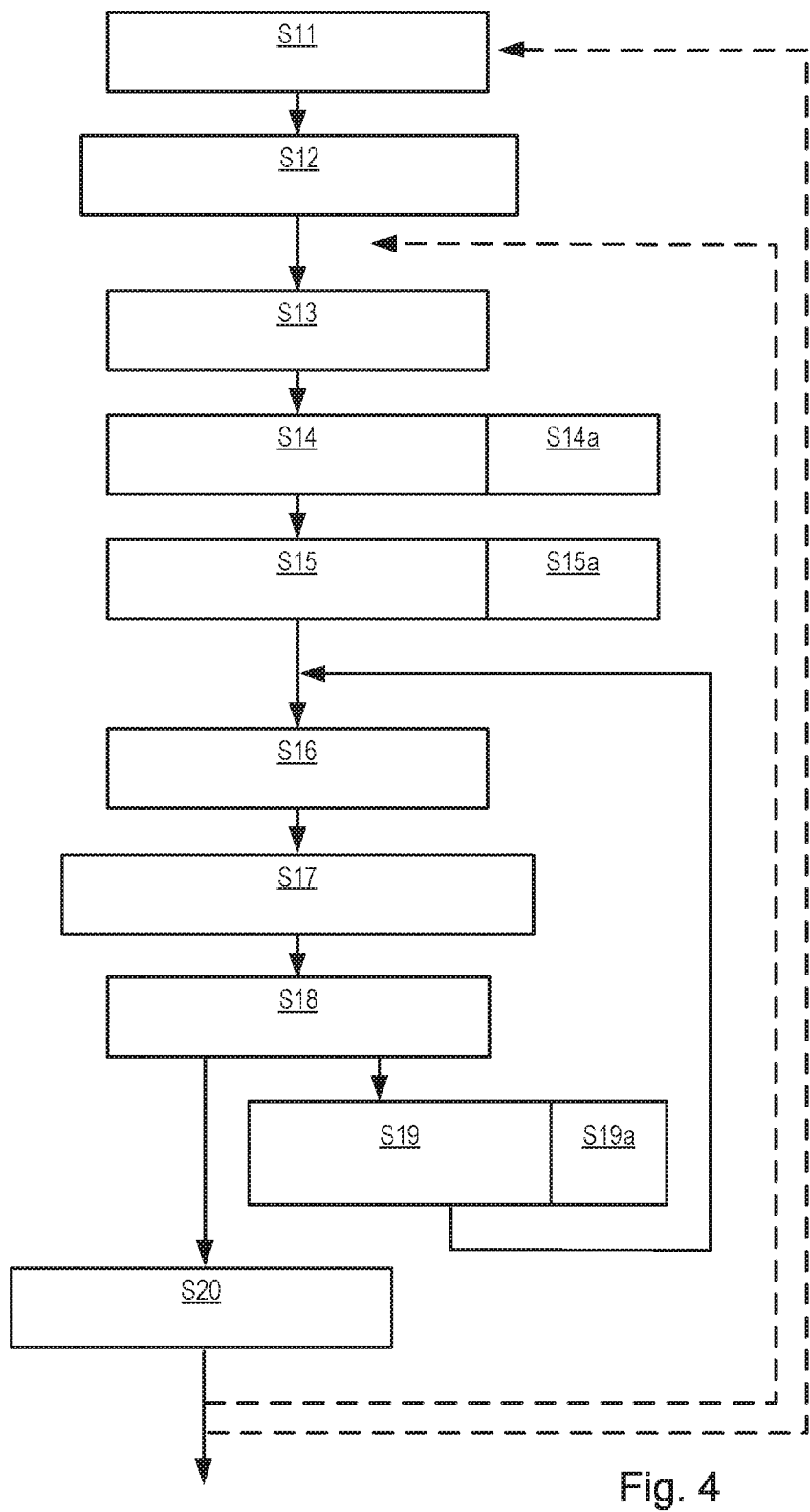
FIG. 4 is a flow chart illustrating a metrology method according to an embodiment of the present invention.

FIG. 4 is a flowchart of a method of measuring parameters of a target structure, using for example the above metrology apparatus 240 and/or 244 and simulation methods disclosed herein. As described above, the target structure may be on a substrate such as a semiconductor wafer. This target will often take the shape of a periodic series of lines in a grating, or structures in a 2-D array. The purpose of the metrology techniques is to measure one or more parameters of the shape by calculation from the observed interaction with radiation. In the reconstruction techniques disclosed herein, rigorous diffraction theories are used effectively to calculate what values of these parameters will result in a particular observed diffraction spectrum. In other words, target shape information is obtained for parameters such as CD (critical dimension) and overlay. Overlay metrology is a measuring technique in which the overlay of two targets is measured in order to determine whether two layers on a substrate are aligned or not. CD, or critical dimension, is the width of the object that is "written" on the substrate and is the limit at which a lithographic apparatus is physically able to write on a substrate. In some situations, the parameter of interest may be CD uniformity, rather than an absolute measurement of CD itself. Other parameters such as edge placement error (EPE), layer height (thickness) and side wall angle (SWA) may also be measured, if desired. Any parameter of the shape that has an influence on the diffraction pattern (scatter spectrum) can in principle be measured in this way. Parameters of interest may also include a parameter related to properties of the material within the structure, rather than the shape of the structure.

Using results from one or both of the metrology apparatuses 240 and 244 in combination with modeling of a target structure T and its diffraction properties, measurement of the shape and other parameters of the structure can be performed in a number of ways. In a first type of process, represented by FIG. 4, a scatter spectrum based on a first estimate of the target shape (a first candidate structure) is calculated and compared with the observed spectrum. Parameters of the model are then varied systematically and the diffraction re-calculated in a series of iterations, to generate new candidate structures and so arrive at a best fit. In a second type of process, spectra for many different candidate structures are calculated in advance to create a "library" of spectra. Then the spectrum observed from the measurement target is compared with the library of calculated spectra to find a best fit. Both methods can be used together: a coarse fit can be obtained from a library, followed by an iterative process to find a best fit.

The terms "spectrum" and "spectra" in this context may refer to a frequency-resolved spectra in the spectroscopic scatterometer of FIG. 2, or to scatter spectra and diffraction patterns in the angle-resolved scatterometer of FIG. 3. The term "scatter spectrum" or "scatter pattern" is particularly useful when the sensor captures only zero order scattered radiation. If the apparatus captures higher diffraction orders, then the scatter pattern may be more commonly referred to as a diffraction spectrum or diffraction pattern.

A third type of process omits the step of modelling the structure and its interaction with inspection radiation, and applies machine learning to correlate features of the observed scatter spectra with parameters of the structure. Machine learning can be based on a training set of spectra observed from real structures, coupled with direct measurements of parameters of the structure, that will be the unknown parameters in a future measurement. Machine learning can also be based on a training set of spectra obtained by modeling (simulation) of the interaction with mathematically modeled structures, as used in the "library" process described above. Training data based on simulation and training data based on real observations can be combined into a larger training set, as desired.

Returning to the first type of process, purely by way of example, the way the measurement of the target shape and/or material properties may be carried out using an angle-resolved scatterometer will be described in summary, with reference to FIG. 4. The following steps are performed. The steps will be listed here, and then explained in more detail:

S11: Receive Substrate with Target(s)
S12: Define Measurement Recipe
S13: Measure Scatter Patterns
S14: Define Model Recipe
S15: Estimate Shape Parameters
S16: Calculate Model Scatter Patterns
S17: Compare Measured v Calculated Patterns
S18: Calculate Merit Function
S19: Generate Revised Shape Parameters
S20: Report Final Shape Parameters At S11 a substrate W is received with one or more metrology target structures T upon it. The target structure will be assumed for this description to be periodic in only one direction (1-D structure). In a case where it is periodic in two directions (2-dimensional structure), or not completely periodic, the processing will be adapted accordingly.

At S12 a measurement recipe is defined. The recipe may define any number of parameters of the illumination and detection settings to be used in a particular application. The recipe may specify one or more combinations of wavelength and polarization for the incident radiation. The recipe may define specific angular distribution for the illumination and detection. The recipe may specify intensity and exposure time of the incident radiation. For example also, phase or coherence of the source(s) could be part of the measurement recipe.

At S13 with a target structure positioned at the spot S, scatter spectra of the structure on the substrate are measured using the apparatus of the general type illustrated in FIG. 4. The measured spectra are captured by pupil image sensor 19 and forwarded to a calculation system within processing unit PU. To obtain a robust measurement through reconstruction, several spectra of the same target may be captured with different sub-recipes. The spectra captured in this way constitute observation data from which properties of the target structure can be determined, whether directly or indirectly.

Note that the observation data may be processed as detailed spectra, or they may be simplified into a set of parameters before being used in calculations. As a particular example, a diffraction pattern may be reduced simply to a set of values representing the intensity of identifiable diffraction orders. The intensity may be obtained for example by identifying a peak in the diffraction spectrum that corresponds to a respective diffraction order, and assigned to that diffraction order a value corresponding to the height of the observed peak. In other cases, all pixels of a scatter pattern may be of interest.

At S14 a 'model recipe' is established which defines a parameterized model of the target structure in terms of a number of parameters $p_i$ ($p_1$, $p_2$, $p_3$ and so on). These parameters may represent for example, in a 1-D periodic structure, the angle of a side wall, the height or depth of a feature, the width of the feature. Properties of the target material and underlying layers are also represented by parameters such as refractive index (at a particular wavelength present in the inspection radiation beam). Importantly, while a target structure may be defined by dozens of parameters describing its shape and material properties, the model recipe will define many of these to have fixed values, while others are to be variable or 'floating' parameters for the purpose of the following process steps. For the purposes of describing FIG. 4, only the variable parameters are considered as parameters $p_i$. Variable parameters will generally include the parameter of interest (the property to be measured), as well as so-called "nuisance" parameters. These are parameters that are correlated with the parameters of interest and may also influence the observed spectra. Automated methods of optimizing the selection of fixed and floating parameters are described in the prior art, for example in US20120123748.

Conventionally, it is assumed that the parameters of the structure model, even the variable parameters, do not vary over the course of an exposure with inspection radiation. On the other hand, in accordance with the principles of the present disclosure, this assumption may not be valid in all cases. Modifications of the method will be discussed further below, that take account of variation of the parameters in the course of the exposure. The conventional steps of the method will be described first of all.

At S15 a model target shape is estimated by setting initial values $p_i(0)$ for the floating parameters (i.e. $p_1(0)$, $p_2(0)$, $p_3(0)$ and so on). Each floating parameter may be generated with certain constraints, as defined in the recipe.

At S16, the parameters representing the estimated shape, together with the properties of the different materials in the model, are used to calculate the scattering properties, for example using a rigorous optical diffraction method or other solver of Maxwell equations, described in the prior art. This gives an estimated or model diffraction pattern of the estimated target shape, for a given combination of wavelength, polarization, angular distribution and so forth.

At S17 and S18 the measured diffraction patterns and the model diffraction patterns are then compared and their similarities and differences are used to calculate a "merit function" for the model target shape.

Assuming that the merit function indicates that the model needs to be improved before it represents accurately the actual target shape, control passes to step S19 where new parameters $p_1(1)$, $p_2(1)$, $p_3(1)$, etc. are estimated and fed back iteratively into step S16. Steps S16 to S18 are repeated. In order to assist the search, the calculations in step S16 further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

When the merit function indicates that this iterative process has converged on a solution with a desired accuracy, control passes to step S20 and the currently estimated parameters (for example a CD value) are reported as the measurement of the actual target structure.

Once the value for one target has been calculated, a new target on the same substrate or a similar substrate may be measured using the same steps S13 etc., without changing the measurement recipe. Where a different type of substrate or target is to measured, or in any case where it is desired to change the measurement recipe, control passes to step S11 or S12 instead.

FIG. 5 illustrates the application of a measurement method (for example the method of FIG. 4) in the management of a lithographic manufacturing system. The steps will be listed here, and then explained in more detail:

S21: Process wafer to produce structures on substrate
S22: Measure CD and/or other parameter across substrate
S23: Update metrology recipe
S24: Update lithography and/or process recipe At step S21, structures are produced across a substrate using the lithographic manufacturing system. At S22, the metrology apparatus 240 and/or 244 and optionally other metrology apparatus and information sources are used to measure a property of the structures across the substrate. A property we are interested in may be one of CD, OVL and or EPE for example. Another application of the method is hotspot- and defect inspection, for example using lensless EUV imaging. At step S23, optionally, metrology recipes and calibrations of the metrology apparatuses are updated in light of the measurement results obtained. For example, where the additional metrology apparatus 244 has a lower throughput than the optical metrology apparatus 240, a few accurate measurements using shorter wavelengths can be used to improve the calculation of measurements made using the optical metrology apparatus, for a specific substrate design and process.

At step S24, measurements of CD or other parameters are compared with desired values, and used to update settings of the lithographic apparatus and/or other apparatus within the lithographic manufacturing system. By providing a metrology apparatus operating at shorter wavelengths, product features and/or product-like features can be measured directly, even at the smallest technology nodes, and in-die targets can be provided and measured without losing too much area. These shorter wavelengths may be for example below 400 nm (broadly UV waveband), optionally below 200 nm (broadly DUV), below 100 nm (broadly EUV), below 10 nm (EUV & soft x-ray), below 1 nm (EUV & soft x-ray) or below 0.1 nm (hard x-ray).

Taking Account of Time-Varying Parameters

As mentioned above, the conventional metrology methods assume that the structure being measured remains constant during the exposure to the inspection radiation. At optical wavelengths, used in conventional scatterometers, this assumption generally holds true, because the photons of the inspection radiation are not energetic enough to cause physical or chemical changes in the materials of the structure or the underlying substrate.

When moving to shorter wavelengths, moreover, a higher energy dose of radiation is required to achieve good reproducibility of measurement results. This is because the signal to noise ratio in respect of photon shot noise equals the square root of the number of photons detected. Therefore, a certain number of photons, rather than a certain energy is required to achieve a desired signal-to-noise ratio. At the same time, at shorter wavelengths, the energy per photon is proportionately higher than in the infrared and visible ranges. Therefore the radiation dose per exposure may be substantially higher than in conventional metrology. In addition, when the photon energy is higher than relevant molecular and atomic binding energies (>>1 eV) many different interaction mechanisms can play a role that do not occur with visible or IR photons. For example, hard x-rays can eject core electrons via the photoelectric effect, and this could lead to secondary electrons via the Auger effect. A person skilled in the art will appreciate that there are more interaction schemes that can occur, depending on the photon energy and the material properties. In this way, a single high energy photon can cause a cascade of events, leading to large chemical or structural changes in the irradiated material.

This high radiation dose in practice causes the structure to change in the course of the exposure. In the case of inspection based on a developed resist pattern, known as after development inspection or ADI, shrinkage of the resist may commonly occur. This is a phenomenon that has already been observed and modeled in detail in the context of patterning using EUV radiation. Even at more conventional wavelengths longer than 400 nm, changes have been observed to occur, which may be due to bleaching of the resist. These changes, when they alter the shape or material properties of the structure in the course of the measurement, can cause inaccuracy in the reported measurement results. Even if a measurement is very accurate as to the dimensions that a structure has during or after the measurement, it may not be useful if the aim is to measure the dimensions of the structure, as it was prior to measurement. Additionally, since it may be desired to make measurements of the same structure at different wavelengths, even if a current observation may be made using inspection radiation which has negligible effect on the structure, the structure may already have been changed by inspection radiation used for a previous observation on the same structure. If this change is not taken into account, it is difficult to obtain an accurate measurement of the structure, as it existed prior to any observation.

FIG. 6 illustrate the effect of radiation on developed resist patterns, which has been referred to as resist "shrinkage". At (a) there is illustrated a typical height profile of a feature 600 formed in developed resist. The feature has a height h and a line width or critical dimension CD. Inspection radiation 602 impinges on the structure during exposure in the metrology apparatus 244. After exposure, as illustrated at (b), the resist material has shrunk, and consequently the feature 600 has a distorted shape, with a reduced height h' and a reduced line width CD'.

FIG. 7(a) illustrates the change in a parameter such as CD (vertical axis) as a function of exposure dose E (horizontal axis). Depending on the radiation intensity, the horizontal axis represents the duration of the exposure, in which the dose per unit time is integrated. Starting at zero dose, a number of dose levels E1, E2 etc. are marked on the horizontal axis, with no particular units. At zero dose, the CD is initially at a value labeled CD0. Up to the dose level E1, no significant change in dimensions is observed. However, as the dose increases through levels E2, E3 and E4, the material of the structure progressively shrinks. At higher doses, no further shrinkage occurs, and the minimum dimension stabilizes at a value labeled CD7.

The chemical and physical mechanisms that cause resist shrinkage are described in more detail in the reference Liu et al., mentioned in the introduction. It should be noted that shrinkage of resist material is not the only change that can be brought about by the dose of inspection radiation. Other materials, for example amorphous carbon, may also be affected. Accordingly, these concerns do not only arise in after development inspection ADI, but also in after etch inspection or AEI. Layer heights may change, in addition to or instead of feature widths. These dimensional changes are not the only types of changes that may be expected, either. As the radiation may cause changes in amorphous or crystal structures, it will be appreciated that material properties such as refractive index n and complex refractive index k might also change. These parameters also influence the interaction of the inspection radiation with the product. In all such cases, the actual shape and/or the apparent shape of the structure under investigation can change in the course of an inspection exposure. Just as in the case when a subject of the photograph moves during a long exposure, the result of shrinkage or other time-based variations in the structure under inspection causes the obtained spectra to be similarly "blurred". This effect inevitably introduces errors and/or increases uncertainty in the measurement results obtained, whether by reconstruction or otherwise.

Of course, if the desired measurement accuracy can be obtained with the dose corresponding to level E1 in FIG. 7, then these changes will have no influence on the measurement results. In practice, however, the dose required for accurate measurement in a number of relevant applications falls in or beyond the part of the curve in which the dimensional change or other change occurs. Consequently, a reconstruction or other calculation will deliver an answer that the CD (for example) value is lower than the actual CD of the feature, prior to measurement. According to the present disclosure, these dimensional and/or other changes are taken into account when calculating a value for the parameter of interest, so that the true, initial value of a parameter can be more accurately reported as a property of the structure under investigation.

To improve accuracy of measurements, there is now proposed a method of determining a property of a structure that includes receiving observation data obtained by exposing the structure one or more times with inspection radiation and observing said inspection radiation after interaction with the structure. Based on the observation data, a value for the parameter of interest as a property of the structure is determined. The determination of the parameter of interest is performed taking into account changes in the structure caused by the inspection radiation during an exposure period. The method may include as a preliminary step defining a number of variable parameters to represent the structure, the variable parameters including at least one parameter of interest. The variable parameters may include one or more time-related parameters representing said changes in the structure caused by the inspection radiation during said exposure period.

In order to take account of the changes, one can define a model of the shrinkage or other change effect. The model may assume an exponential change, or a piecewise linear change, similar to the curve seen in FIG. 7(a). The changes can be taken into account even when the observation data is obtained by integration over a single long exposure interval $t_{EXP}$, as illustrated in FIG. 7(b). In a further refinement, however, the exposure interval $t_{EXP}$ can be subdivided into shorter exposures, as illustrated in FIG. 7(c). In the latter case, it will be appreciated that a number of "snapshot" spectra are captured, that can reveal different stages of the change in progress. In the former case, a single, integrated spectrum is obtained, which corresponds to the "blurred photograph" presented above. In either case, by taking the changes in the structure into account, a better measurement of the initial value of the parameter of interest can be expected.

Referring back to FIG. 4, modifications of a reconstruction type measurement method will now be described, by which the above principle may be implemented. The first change is in relation to step S14. As part of the model recipe that describes the structure in terms of fixed and floating parameters, including dimensional parameters and material properties, a step S14a adds to the recipe one or more time-related parameters. One or more of the parameters of interest or floating parameters may be modeled as a time-dependent parameter. As a simple example, a model for measurement of CD could be expressed in the following form:

$$CD(t)=CD_0-S \cdot t$$

where $CD_0$ and S are parameters representing the initial CD and the CD shrinkage per unit time respectively. Parameters $CD_0$ and S could be set fixed or floating independently. In the case of CD measurement, the initial CD labeled $CD_0$ may be the parameter of interest, of course and therefore will be floating. The shrinkage per unit time S may be known in advance from experience, or may be floating within some known range of experience. Parameters $CD_0$ and S can be referred to as time-related parameters, while CD(t) can be referred to as a time-dependent parameter. The CD(t) parameter, together with for example a height h(t) and SWA(t), will then describe the structure during the exposure.

It will be understood that one could come up with much more complicated relations for a time-related parameter such as CD(t). The form of expression and calculation is not limited to mathematical expressions like the one given above, but it could also be tabulated, such as:

$$CD(t) = \begin{cases} CD_0, & t < t0 \\ CD_1, & t1 > t > t0 \\ \ldots \text{etc.} \end{cases}$$

or expressed in relation to other time-dependent parameters, for example:

$$CD(t) = \frac{h(t)}{2} + CD_0$$

These time-related parameters may equally be considered as dose-related parameters, and the radiation intensity and/or energy per photon (or wavelength) may be fixed or variable parameters of the model also.

In step S15a, initial values for these time-related parameters are set, at the same time as initial values for the other parameters of the model. Steps S16 to S18 proceed just as described above, ending with a judgment whether the shape and time-related parameters fit well the observed spectrum or spectra. If another iteration is required, in step S19a, revised time-based parameters may be generated. By the iterative process, a best fit is obtained, in which not only fixed properties of the material and shape of the structure are taken into account, but also variations in the shape or material of the structure that occur over time, during an exposure period.

FIG. 8 illustrates a modified version of the method of FIG. 4, using multiple captures over subdivisions of the overall exposure interval $t_{EXP}$, in the manner illustrated in FIG. 7(c). All the steps are the same, except that the steps S13 to S19 with regard to a number of snapshots obtained over subdivisions of the overall exposure interval $t_{EXP}$. Thus, in step S13, multiple captured images are received allowing the change of the scatter spectrum over time to be resolved. Similarly, in defining the model recipe and setting initial values for the parameters at steps S14 and S15, the model can have parameters that differ between different subdivisions of the exposure interval. The model may even have a different structure for different sub-intervals. For example, you might want to use two different models for the shapes shown in FIGS. 6 (a) and (b). The shape in FIG. 6 (a) can be modelled as just a rectangle, which is often easier to deal with from a computational point of view. The distorted shape shown in FIG. 6 (b) can be modelled as a trapezoid, or by something much more complicated, depending what level of accuracy is required to achieve a desired accuracy in the parameters of interest. For example the shape in FIG. 6 (b) can be modeled as a number of b-spline curves, which are then staircased to fit in the forward scattering model used in step S16. This will also require some kind of conversion between the rectangle parameters and the b-spline parameters.

As a consequence of the inclusion of time-related parameters and time-dependent parameters, in the calculation of model spectra at step S16, the model can result in a different spectrum in different sub-intervals, reflecting changes in the structure. In the comparing of measured and calculated spectra, better matching can be expected (once the time-based parameters of the model are matched well with the real changes happening in the structure). In step S18, individual merit functions can be obtained for each sub-interval, as well as an overall merit function. When all parameters are matched with reality, the merit function scores will be uniformly good. If the score is good in some sub-intervals and bad in others, this information can be used in step S19a to generate revised values for the time-related parameters. More generally, the quality of fitting of simulation and observation can be used as a measure of the correctness of the time-based model and parameter values.

In addition to subdividing an exposure into a number of sub-intervals, it will be appreciated that multiple exposures may be used, for example to obtain spectra using different wavelengths of inspection radiation, or different polarizations, different incidence angles and so on. Unless a different target structure is used of reach of these, which is generally undesirable, the dose of radiation incident on the structure will accumulate over the series of exposures. The same method as illustrated above and as shown in FIG. 7(c) can be applied in that case, so as to take into account radiation-induced changes in the structure, when comparing spectra obtained using different wavelengths. The different exposures of the same structure may be made for measuring the same property, or different properties.

As mentioned already above, a reconstruction method such as that illustrated in FIG. 4 and FIG. 8 is not the only method to derive a value for one or more properties of the target structure based on observation data from a metrology apparatus. A library based method can be used. A machine learning method can be used, using a training set of spectra and measurements. The training set of spectra may include a library of simulated spectra and/or real observed spectra, combined with measurement data obtained by other means, such as SEM. Compared with the parameter adviser function described above, use of machine learning will allow effectively a free assignment of fixed and floating parameters in different parts of the parameter space, for example using Minimum Mean Squared Error. This has the advantage that the model recipe can be optimized for each part of the parameter space, rather than a single recipe being optimized over the whole parameter space. Coupled with taking into account time-based changes, overall accuracy of the reported measurements can be improved.

The principles of the present disclosure can be applied in other types of analysis. For example, asymmetry is a parameter that can be measured for a range of applications, notably overlay. As mentioned above, asymmetry can be measured in the pupil image, for example to measure overlay as a parameter of interest. Asymmetry of small targets can be measured by dark-field imaging, and not only pupil imaging. Multiple biased grating structures can be measured in a single image. Targets can be designed so that parameters such as dose and focus can be measured through measurement of asymmetry, and not only overlay.

Some care is of course required in adapting the calculations to allow for changes in the structure during the measurement exposure. Considering a change such as shrinkage, if the shrinkage is symmetrical then the shrinkage will drop out in an asymmetry measurement. However, shrinkage does not necessary need to be symmetrical, so that shrinkage can be a source of asymmetry, leading to inaccuracy in measurement of asymmetry-related parameters. The impact of shrinkage induced asymmetry can be suppressed by taking it into account in the algorithm that is used to calculate overlay or other parameter of interest. Such a suppression could be based on suppressing asymmetries that are a function of time, this is a possibility if more than one measurement is done. If just one measurement is done, one can simply design or train the algorithm to be insensitive to asymmetries occurring due to shrinkage. This design or training could be done for example by means of modelling the time-related component of asymmetry, or measuring it, or a combination of both.

Application Examples—EUV Metrology Apparatuses

FIG. 9 illustrates schematically an apparatus 900 for performing High-resolution lensless imaging using EUV radiation reflected from the target structure. More detail of this apparatus and method is provided in pending patent application EP15180807.8, mentioned in the introduction. The context of that application is hereby incorporated by reference. Lensless imaging can be performed by calculating the image from one or more recorded diffraction patterns, without a physical imaging system. A product structure 907 is formed with defects that are to be detected by the lensless imaging. A spot (S) of EUV radiation which is at least partially coherent is provided on the product structure while a detector 908 captures at least one diffraction pattern formed by the radiation after scattering by a product structure 907. At least one synthetic image of the product structure is calculated from the captured image data by a processor 910.

Processor 910 may implement a method of the type disclosed above to simulate interaction of the EUV radiation with the target structure. The method may be used in a reconstruction context as illustrated in FIG. 4, or in some other context. For defect metrology, the synthetic image may be compared with reference data that describes a nominal product structure. In one embodiment, the lensless imaging technique used is ptychography. A number of diffraction patterns are obtained using a series of overlapping spots (S, S'), and the synthetic image is calculated using the diffraction patterns and knowledge of the relative displacement. The EUV radiation may have wavelengths in the range 5 to 50 nm, close to dimensions of the structures of interest. The radiation source 912 may be for example a higher harmonic generator (HHG) source based on a laser and HHG cell.

In all of the processing performed by processor 910 to generate the desired image or other representation of the structure, changes in the structure that are caused by doses of inspection radiation can be taken into account to improve accuracy of imaging the original structure.

FIG. 10 illustrates schematically another metrology apparatus based on reflection of x-ray and/or EUV radiation generated using an inverse Compton scattering source. More detail of this apparatus and method is provided in pending patent application EP15180740.1, mentioned in the introduction. The context of that application is hereby incorporated by reference. Using the inverse Compton scattering source, X-ray, EUV, UV and VIS radiation can be generated with high brightness and rapid frequency switching. In the drawing, a target structure (T) made by lithography or used in lithography is inspected by irradiating the structure at least a first time with EUV radiation 1004 generated by inverse Compton scattering source 1030. In this type of source a high energy electron beam interacts with a laser beam in a cavity to generate output radiation at x-ray or longer wavelengths. Radiation 1008 scattered by the target structure in reflection or transmission is detected by detector 1012 and properties of the target structure are calculated by a processor 1040 based on the detected scattered radiation.

Processor 1040 may implement a method of the type disclosed above to simulate interaction of the EUV radiation with the target structure. The method may be used in a reconstruction context as illustrated in FIG. 4, or in some other context. The radiation may have a first wavelength in the EUV range of 0.1 nm to 125 nm. Using the same source and controlling an electron energy, the structure may be irradiated multiple times with different wavelengths within the EUV range, and/or with shorter (x-ray) wavelengths and/or with longer (UV, visible) wavelengths. By rapid switching of electron energy in the inverse Compton scattering source (330), irradiation at different wavelengths can be performed several times per second. Performing reconstruction with information from different wavelengths can resolve ambiguities that would otherwise be present in solving the Maxwell equations.

Again, whatever method of processing is performed to determine the property of the structure that is under investigation, changes caused by doses of inspection radiation can be taken into account to improve accuracy of the result.

Also to improve accuracy, measurements made with two or more types of apparatus can be obtained in a variety of hybrid techniques. If the same target is used for multiple measurements, it is clear that cumulative changes of induced by the inspection radiation from the different apparatuses can be taken into account to improve the accuracy of the result. More details of the metrology apparatuses can be found in the patent applications referred to above. It will be understood that they are only examples of the many types of apparatuses and methods in which the techniques disclosed herein may be applied. Any or all of these types of apparatuses can be used in a given application, whether for semiconductor manufacturing or other purposes.

Further embodiments according to the invention are described in below numbered clauses:

1. A method of determining a property of a structure, the method including the steps of:
(a) defining one or more variable parameters to represent the structure, the variable parameters including at least one parameter of interest;
(b) receiving observation data obtained by exposing the structure one or more times with inspection radiation and observing said inspection radiation after interaction with the structure; and
(c) based on the observation data, determining a value for the parameter of interest as a property of the structure, wherein the determination of the parameter of interest is performed taking into account changes in the structure caused by the inspection radiation during an exposure period.

2. A method according to clause 1 wherein the variable parameters include one or more time-related parameters representing said changes in the structure caused by the inspection radiation during said exposure period.

3. A method according to clause 2 wherein step (c) further includes determining a value for one or more of said time-related parameters.

4. A method according to clause 2 or 3 wherein at least one of said time-related parameters represents a dimensional change caused by the inspection radiation in a part of the structure.

5. A method according to clause 2, 3 or 4 wherein at least one of said time-related parameters represents a change of an optical property caused by the inspection radiation in a part of the structure.

6. A method according to any preceding clause wherein the step (c) takes account of intensity of the inspection radiation in combination with duration of said exposure period.

7. A method according to any preceding clause wherein the observation data represents interaction of the inspection radiation with the structure accumulated over said exposure period.

8. A method according to any preceding clause wherein the observation data represents interaction of the inspection radiation with the structure separately for a plurality of sub-periods of an exposure period.

9. A method according to any preceding clause wherein the determination of the parameter of interest is performed taking into account changes in the structure caused by the inspection radiation during an exposure period related to a previous observation of the same structure.

10. A method according to any preceding clause wherein the structure is made by lithography alongside or as part of a semiconductor device.

11. A method according to any preceding clause wherein in step (c) the parameter of interest is determined at least partly using machine learning, based on real and/or simulated observation data obtained from different structures.

12. A method according to any preceding clause wherein step (c) includes:
(c1) simulating interaction of inspection radiation with the structure with a given set of values for said variable parameters; and
(c2) comparing the interaction simulated in step (c1) with the observation data;
(c3) varying one or more parameters of the structure based on the result of the comparison;
(c4) repeating step (c1) using the varied parameters; and
(c5) after a number of iterations of steps (c1) to (c4), reporting a value for the parameter of interest.

13. A method according to any preceding clause wherein the inspection radiation has a wavelength shorter than 400 nm.

14. A method according to any preceding clause wherein the inspection radiation has a wavelength shorter than 100 nm.

15. A processing apparatus for determining a property of a structure, the processing apparatus comprising:
storage for one or more variable parameters to represent the structure, the variable parameters including at least one parameter of interest;
storage for receiving observation data obtained by exposing the structure one or more times with inspection radiation and observing said inspection radiation after interaction with the structure; and
a processor arranged to use the observation data to determine a value for the parameter of interest as a property of the structure, taking into account changes in the structure caused by the inspection radiation during an exposure period.

16. A processing apparatus according to clause 15 wherein the processing apparatus is arranged to receive and use observation data representing interaction of the inspection radiation with the structure separately for a plurality of sub-periods of an exposure period.

17. A processing apparatus according to clause 15 or 16 wherein the processor is arranged to take into account changes in the structure caused by the inspection radiation during an exposure period related to a previous observation of the same structure.

18. A metrology apparatus for use in determining a property of a structure, the metrology apparatus comprising:
an illumination system for generating a beam of inspection radiation;
a substrate support operable with the illumination system for irradiating a structure formed on the substrate with said inspection radiation;
a detection system for detecting the inspection radiation after interaction with the structure; and
a processing apparatus according to clause arranged to determine a property of the structure based on the detected radiation and taking into account changes in the structure caused by the inspection radiation during an exposure period.

19. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the step of measuring the property of the structure includes determining a property by a method according to any of clauses 1 to 14.

20. A lithographic system comprising a lithographic apparatus in combination with a metrology apparatus according to clause 18.

21. A computer program product comprising machine readable instructions for causing a processor to perform a method according to any of clauses 1 to 14.

22. A computer program product comprising machine readable instructions for causing a processor to perform as the processing apparatus according to any of clauses 15 to 17.

CONCLUSIONS

In conclusion, the present disclosure provides metrology methods and apparatuses in which changes caused by the inspection radiation can be taken into account and corrected. The changes can be taken into account as an integral part of the calculations, as described above. Alternatively, the changes can be taken into account afterwards and applied as a correction to a result obtained by a more conventional calculation.

An embodiment of the invention may be implemented using a computer program containing one or more sequences of machine-readable instructions describing methods of controlling the lithographic apparatus. This computer program may be executed for example within the control unit LACU 206 of FIG. 1, the additional metrology apparatus 240 and 244, the supervisory control system 238 or some other controller. There may also be provided a data storage medium (e.g., semiconductor memory, magnetic or optical disk) having such a computer program stored therein. The storage may be of non-transitory type. A programmable processor programmed in this way may be provided as a separate apparatus, remote from the lithographic manufacturing system and the metrology apparatus. The processor only requires in that case to receive the observation data from the metrology apparatus.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 0.1 to 125 nm), as well as x-radiation (0.01 to 1 nm) and particle beams, such as ion beams or electron beams.

The terms "radiation" and "beam" used herein further encompass other forms of radiation including acoustic (sound) radiation. Phenomena of scattering and diffraction arise also in sound, and similar calculations can be performed for reconstruction of unknown structures by acoustic scattering.

The term "lens", where the context allows, may refer to any one or combination of various types of optical components, including refractive, reflective, diffractive, magnetic, electromagnetic and electrostatic optical components.

The breadth and scope of the present invention should not be limited by any of the above-described exemplary embodiments, but should be defined only in accordance with the following claims and their equivalents.

The invention claimed is:

1. A method comprising:
defining one or more variable parameters to represent a structure, the variable parameters including at least one parameter of interest;
receiving observation data obtained by exposing the structure one or more times with inspection radiation and observing the inspection radiation after interaction with the structure; and
based on the observation data, determining a value for the parameter of interest as a property of the structure,
wherein the determination of the parameter of interest is performed taking into account changes in the structure caused by the inspection radiation during an exposure period.

2. The method of claim 1, wherein the variable parameters include one or more time-related parameters representing the changes in the structure caused by the inspection radiation during the exposure period.

3. The method of claim 2, wherein the determining further includes determining a value for one or more of the time-related parameters.

4. The method of claim 2, wherein at least one of the time-related parameters represents a dimensional change caused by the inspection radiation in a part of the structure.

5. The method of claim 2, wherein at least one of the time-related parameters represents a change of an optical property caused by the inspection radiation in a part of the structure.

6. The method of claim 1, wherein the determining takes account of intensity of the inspection radiation in combination with duration of the exposure period.

7. The method of claim 1, wherein the observation data represents interaction of the inspection radiation with the structure accumulated over the exposure period.

8. The method of claim 1, wherein the observation data represents interaction of the inspection radiation with the structure separately for a plurality of sub-periods of an exposure period.

9. The method of claim 1, wherein the determination of the parameter of interest is performed taking into account changes in the structure caused by the inspection radiation during an exposure period related to a previous observation of the same structure.

10. The method of claim 1, further comprising using a lithography device to form the structure alongside or as part of a semiconductor device.

11. The method of claim 1, wherein the parameter of interest is determined at least partly using machine learning, based on real and/or simulated observation data obtained from different structures.

12. A method of claim 1, wherein the determining comprises:
simulating interaction of inspection radiation with the structure with a given set of values for the variable parameters; and
comparing the interaction simulated by the simulating with the observation data;
varying one or more parameters of the structure based on the result of the comparison;
repeating the simulating using the varied parameters; and
after a number of iterations of the simulating, comparing, varying, and repeating, reporting a value for the parameter of interest.

13. A processing apparatus comprising:
storage configured to store one or more variable parameters to represent a structure, the variable parameters including at least one parameter of interest;
storage configured to receive observation data obtained by exposing the structure one or more times with inspection radiation and observing the inspection radiation after interaction with the structure; and
a processor configured to use the observation data to determine a value for the parameter of interest as a property of the structure, taking into account changes in the structure caused by the inspection radiation during an exposure period.

14. The processing apparatus of claim 13, wherein the processing apparatus is configured to receive and use observation data representing interaction of the inspection radiation with the structure separately for a plurality of sub-periods of an exposure period.

15. The processing apparatus of claim 13, wherein the processor is configured to take into account changes in the structure caused by the inspection radiation during an exposure period related to a previous observation of the same structure.

16. A metrology apparatus comprising:
an illumination system for generating a beam of inspection radiation;
a substrate support operable with the illumination system for irradiating a structure formed on the substrate with the inspection radiation;
a detection system for detecting the inspection radiation after interaction with the structure; and
a processing apparatus comprising:
storage configured to store one or more variable parameters to represent a structure, the variable parameters including at least one parameter of interest;
storage configured to receive observation data obtained by exposing the structure one or more times with inspection radiation and observing the inspection radiation after interaction with the structure; and
a processor configured to use the observation data to determine a value for the parameter of interest as a property of the structure, taking into account changes in the structure caused by the inspection radiation during an exposure period,
wherein the processing apparatus is configured to determine a property of the structure based on the detected radiation and taking into account changes in the structure caused by the inspection radiation during an exposure period.

17. A device manufacturing method comprising:
transferring a pattern from a patterning device onto a substrate using a lithographic process, the pattern defining at least one structure;
measuring one or more properties of the structure to determine a value for one or more parameters of the lithographic process; and
applying a correction in subsequent operations of the lithographic process in accordance with the measured property,
wherein the measuring the property of the structure includes determining a property by a method comprising:
  defining one or more variable parameters to represent a structure, the variable parameters including at least one parameter of interest;
  receiving observation data obtained by exposing the structure one or more times with inspection radiation and observing the inspection radiation after interaction with the structure; and
  based on the observation data, determining a value for the parameter of interest as a property of the structure,
  wherein the determination of the parameter of interest is performed taking into account changes in the structure caused by the inspection radiation during an exposure period.

18. A lithographic system comprising:
an illuminator configured to produce a beam of radiation;
a pattering device configured to impart a pattern on the beam of radiation;
a projection system configured to project the patterned beam onto a substrate; and
a metrology apparatus comprising:
  an illumination system for generating a beam of inspection radiation;
  a substrate support operable with the illumination system for irradiating a structure formed on the substrate with the inspection radiation;
  a detection system for detecting the inspection radiation after interaction with the structure; and
  a processing apparatus comprising:
    storage configured to store one or more variable parameters to represent a structure, the variable parameters including at least one parameter of interest;
    storage configured to receive observation data obtained by exposing the structure one or more times with inspection radiation and observing the inspection radiation after interaction with the structure; and
    a processor configured to use the observation data to determine a value for the parameter of interest as a property of the structure, taking into account changes in the structure caused by the inspection radiation during an exposure period,
  wherein the processing apparatus is configured to determine a property of the structure based on the detected radiation and taking into account changes in the structure caused by the inspection radiation during an exposure period.

19. A non-transitory computer program product comprising machine readable instructions for causing a processor to perform an operation comprising:
  defining one or more variable parameters to represent a structure, the variable parameters including at least one parameter of interest;
  receiving observation data obtained by exposing the structure one or more times with inspection radiation and observing the inspection radiation after interaction with the structure; and
  based on the observation data, determining a value for the parameter of interest as a property of the structure,
  wherein the determination of the parameter of interest is performed taking into account changes in the structure caused by the inspection radiation during an exposure period.

* * * * *